(12) United States Patent
Hwang et al.

(10) Patent No.: US 8,465,764 B2
(45) Date of Patent: Jun. 18, 2013

(54) METHOD FOR PREPARING A PHARMACEUTICAL COMPOUND BY WAY OF MAGNETIC CARBON NANOCAPSULES

(75) Inventors: Gan-Lin Hwang, Tainan (TW); Tsung-Shann Jiang, Taishan Township, Taipei County (TW); Shu-Ling Yeh, Yangmei Township, Taoyuan County (TW); Hsien-Ming Wu, Hsinchu (TW); Shu-Hao Lee, Keelung (TW); Shih-Jung Tsai, Hsinchu (TW)

(73) Assignees: Phytohealth Corporation (TW); Industrial Technology Research Institute (TW)

( * ) Notice: Subject to any disclaimer, the term of this patent is extended or adjusted under 35 U.S.C. 154(b) by 1553 days.

(21) Appl. No.: 11/367,349

(22) Filed: Mar. 6, 2006

(65) Prior Publication Data

US 2007/0098780 A1    May 3, 2007

(30) Foreign Application Priority Data

Mar. 8, 2005  (TW) ................. 94107017 A
Mar. 3, 2006  (TW) ................. 95107288 A

(51) Int. Cl.
  *A61K 9/48*    (2006.01)

(52) U.S. Cl.
  USPC .......................................................... 424/452

(58) Field of Classification Search
  USPC .......................................................... 424/452
  See application file for complete search history.

(56) References Cited

U.S. PATENT DOCUMENTS

| | | | | |
|---|---|---|---|---|
| 5,955,100 | A  * | 9/1999 | Bosslet et al. | 424/450 |
| 6,841,509 | B1 * | 1/2005 | Hwang et al. | 502/180 |
| 2003/0064050 | A1 * | 4/2003 | Malik et al. | 424/78.17 |

OTHER PUBLICATIONS

Tsang-Tsan Su, Commercialization of Nanotechnology—Taiwan Experience, Jan. 10-13, 2006, Emerging Technologies—Nanoelectronics, 2006 IEEE Conference, pp. 25-28.*
Reedijk (Cisplatin: sunthesis, antitumor activity and mechanism of action, Pharmaeulisch Weekblad Scientific Edition, vol. 7, pp. 173-180, 1985).*

* cited by examiner

*Primary Examiner* — Frederick Krass
*Assistant Examiner* — Adam C Milligan
(74) *Attorney, Agent, or Firm* — Bacon & Thomas, PLLC

(57) ABSTRACT

A method for preparing a pharmaceutical compound by way of magnetic carbon nanocapsules is disclosed. The method comprises steps of: (a) providing a magnetic carbon nanocapsule with C—$(COOH)_2$ group, and Pt cations, to form a complex; (b) collecting the complex from the magnetic carbon nanocapsule; and (c) removing the Pt cations on the complex.

1 Claim, 12 Drawing Sheets

| # | Peak | Retention time | Area | Percentage | Conc. |
|---|------|----------------|------|------------|-------|
| 0 |      | 3.424          | 74.82 | 11.69     | 0.00  |
| 1 | amb  | 7.301          | 565.26 | 88.31    | 0.00  |

METHOD FOR PREPARING A PHARMACEUTICAL COMPOUND BY WAY OF MAGNETIC CARBON NANOCAPSULES

BACKGROUND OF THE INVENTION

1. Field of the Invention

The present invention relates to a method for preparing pharmaceutical compounds, particularly a method for preparing pharmaceutical compounds by magnetic carbon nanocapsules.

2. Description of Related Art

A carbon nanocapsule is a polyhedron composed of a enclosed multilayer graphite structure, whose diameter ranges from 1 to 100 nm but is usually 30-40 nm. It is able to be stuffed with magnetic metal inside (a carbon nanocapsule stuffed with magnetic metal is referred to as M@CNC hereafter). As to the graphite layer on the shell of a carbon nanocapsule, the central parts are exclusively six-member rings, the corners are composed of five-member rings, and every carbon atom is $sp^2$; the enclosed multilayer graphite structure endows effective protection of the internal metal particles against oxidization and aggregation, allowing magnetism of internal nano metal to be preserved stably. Besides, the surface of the graphite layer shell of the carbon nanocapsule can be chemically modified, making it disperse in a solvent easily, ready to use, and have stronger affinity. Cis-platinum anticancer drug Cisplatin is widely used to fight against cancer, but because the required material, PtCl4, is very expensive, the manufacture costs of Cisplatin-series anticancer drugs have been high, and the price depends on the yield of the method used for preparation. For methods of prior arts, cis-form and trans-form compounds usually coexist in the products, making it uneasy to purify desired cis-form compounds used to prepare drugs, which often leads to low yields. To avoid formation of trans-form compounds, the prior arts usually need extra steps of preparation in order to raise the proportion of cis-compounds.

There are various ways to prepare cisplatin-series anticancer drugs and the analogs thereof. The yields are usually 28-70% with current techniques. The following formulas exemplifies methods of synthesis known in the art:

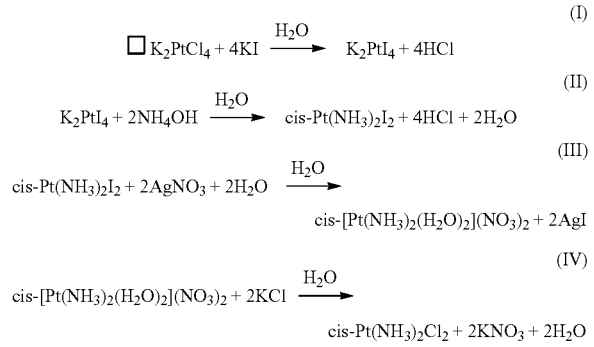

Yields of Cisplatin synthesized by the above procedures are low because of the occurrence of cis-form compounds, which are capped at 70%. Thus, to improve yields in order to lower the costs of drug manufacturing, developing a novel and cheap method of preparation is necessary.

SUMMARY OF THE INVENTION

The present invention employs carbon nanocapsules filled with magnetic metal as the carriers of synthesis of Cisplatin, which are stereo-selective and characterized by the ability to be recycled magnetically.

The present invention relies on the principles that magnetic carbon nanocapsules can be recycled and controlled magnetically, and that [C(—COOH)$_2$] group pairs on their surfaces are easy to be modified and chelate easily with platinum, to make them the carriers for synthesis of Cisplatin. Cisplatin is a commonly used agent in chemotherapy. The present inventions developed novel synthesis steps and improved the yield of Cisplatin preparation.

The present invention is a method for preparation of pharmaceutical compounds using magnetic carbon nanocapsules, comprising steps of: (a) providing platinum cations and carbon nanocapsules having C—(COOH)$_2$ groups to form a complex; (b) collecting the complexes from the magnetic carbon nanocapsule; and (c) removing the platinum ion on the complex.

The platinum ion of step (a) of the present invention is quadridentate, which forms bonds with the [C(—COOH)$_2$] groups on the carbon nanocapsule on one side and with two chloride ions on the other side (Fe@CNC—[C(COO—)$_2$ PtCL$_2$]$_n$b). In step (b), collection of complexes can be performed by any method known in the art Preferably, the collection is done by magnetism, gravity forces, or centrifugal forces. The method of the present invention can further comprise a step (b1), which follows step (b), proceeding with amination on collected complexes. By way of the amination, NH$_2$ replaces chloride ions of the complexes. In step (c), it is preferred to remove platinum on the complexes through hydrolysis. Meanwhile, to fully utilize costly platinum, a step (d) recovering the platinum on the complexes is preferably taken.

The assembly of the magnetic carbon nanocapsule suitable to the method of the present invention can be an outer shell having enclosed multilayer graphite structure and magnetic metals comprised inside thereof, thereby forming a polyhedral carbon cluster. Magnetic metal comprised in the magnetic carbon nanocapsule can be Fe, Co, Ni or the alloy thereof. Preferably, the diameter of the magnetic carbon nanocapsule is in a range of 3-100 nm. More preferably, the diameter of the magnetic carbon nanocapsule is in a range of 30-40 nm. By using the method of the present invention, the Cisplatin-series drugs (including cisplatin and dihydrate cisplatin) can be prepared.

Other objects, advantages, and novel features of the invention will become more apparent from the following detailed description when taken in conjunction with the accompanying drawings.

DETAILED DESCRIPTION OF THE PREFERRED EMBODIMENT

The techniques to synthesize cisplatin drugs disclosed in the present invention employ [C(—COOH)$_2$] group pairs on the magnetic carbon nanocapsules (M@CNC) to form coordinate bonding with platinum cations and form stable complex intermediates. The M@CNC—[C(COO—)$_2$PtCl$_2$] complexes are possible to be reused by magnetic recycling, so as to avoid loss of expensive platinum and improve usage of platinum.

Examples 1

First, a —COOH pair on the magnetic carbon capsule is modified and the —COOH group pair are sure to form a stable cis-form complex intermediate with PtCl4; the Fe@CNC—[C(COO—)$_2$ PtCl$_2$]$_n$ complex is possibly to be reused by magnetic recycling to avoid loss of expensive platinum, so as to improve the usage of platinum. Subsequently, Cl on the Fe@CNC—[C(COO—)$_2$PtCl$_2$]$_n$ complex is replaced with NH$_2$, resulting in a Fe@CNC—[C(COO—)$_2$Pt(NH$_3$)$_2$]$_2$]$_n$ complex. Finally, platinum is removed by hydrolysis and Pt(NH$_2$)Cl$_2$ is obtained. Fe@CNC carrier can be recycled and reused, and Pt(NH$_2$)Cl$_2$ products are ensured to be cis-form due to the steric effect of a [C(—COOH)$_2$] group pair thereon.

Example 2

Figure 1:
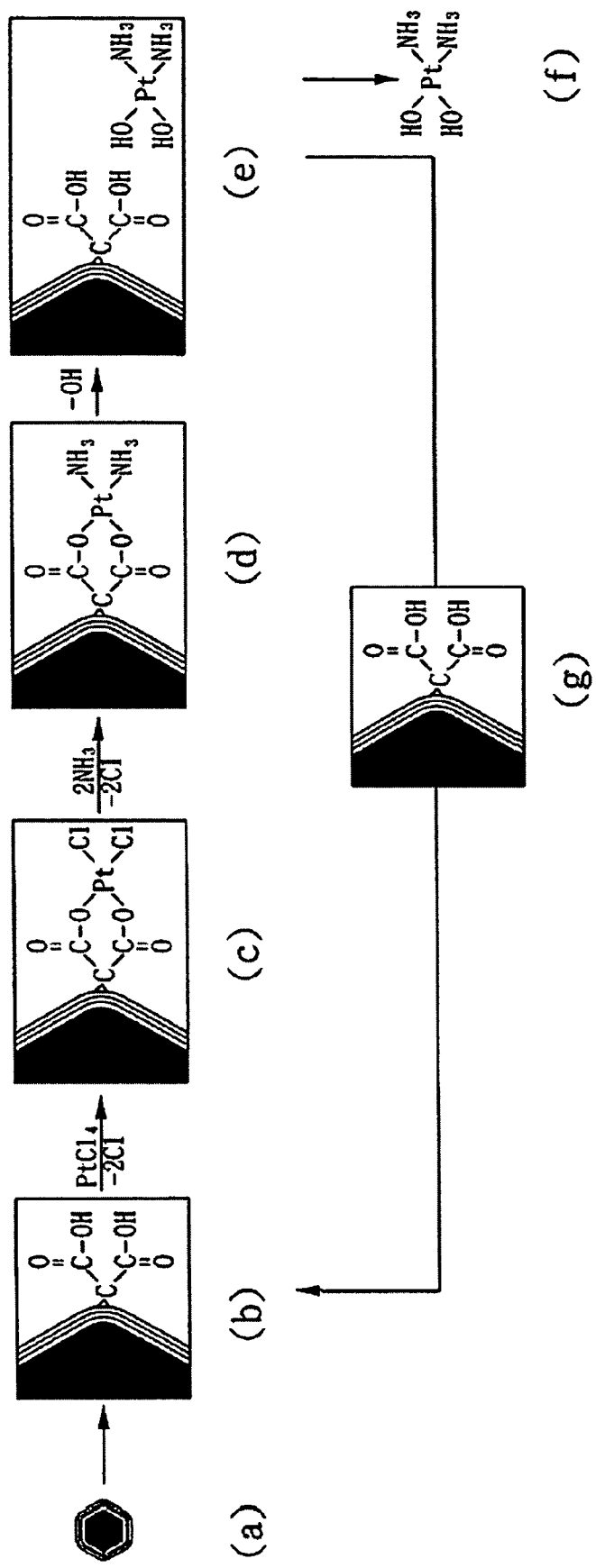
FIG. 1 is the flow chart of the method of the present invention.
Figure 11:
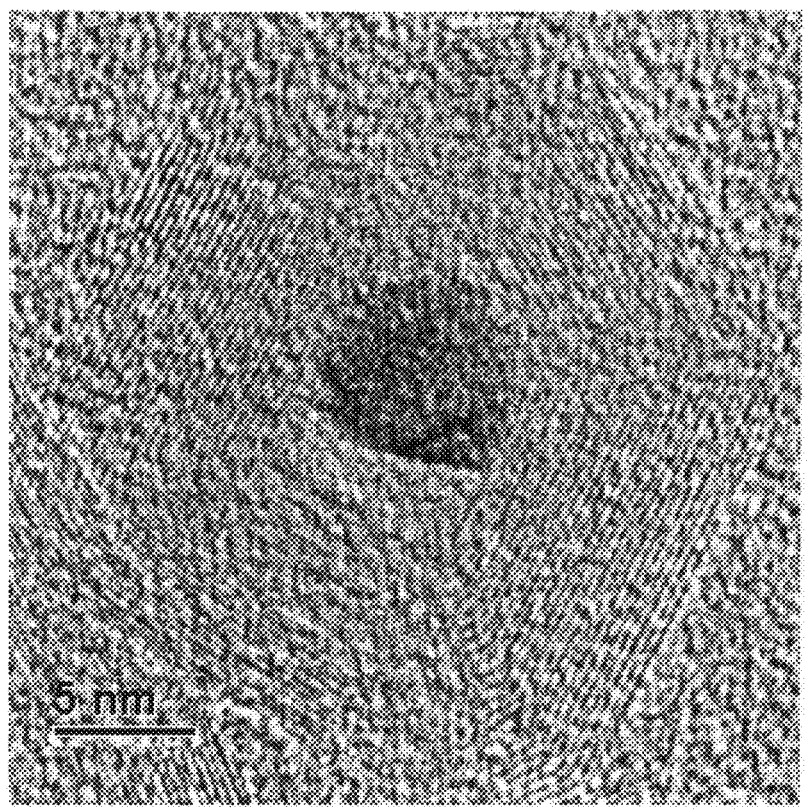
FIG. 11 is the TEM photograph of carbon nanocapsules filled with magnetic metal.

Experimental procedures are shown in FIG. 1, and each step is explained in details as follows:

Step 1. Modification of Functional Groups on the Surface of the Carbon Nanocapsule 0.5 g of carbon nanocapsules (as shown in FIG. 11) are added with 1l of diethyl bromomalonate, and 12.5 g of 1,8-Diazabicyclo[5.4.0]undec-7-ene. Toluene (15 ml) was used as a solvent. Then the product Fe@CNC—[C(COOEt)$_2$]$_n$ was dried.

The dried product Fe@CNC—[C(COOEt)$_2$]$_n$ was put into diluted hydrochloric acid and is refluxed for 4 hours. Then carbon nanocapsules containing [C(—COOH)$_2$] group pairs were obtained.

Figure 2:
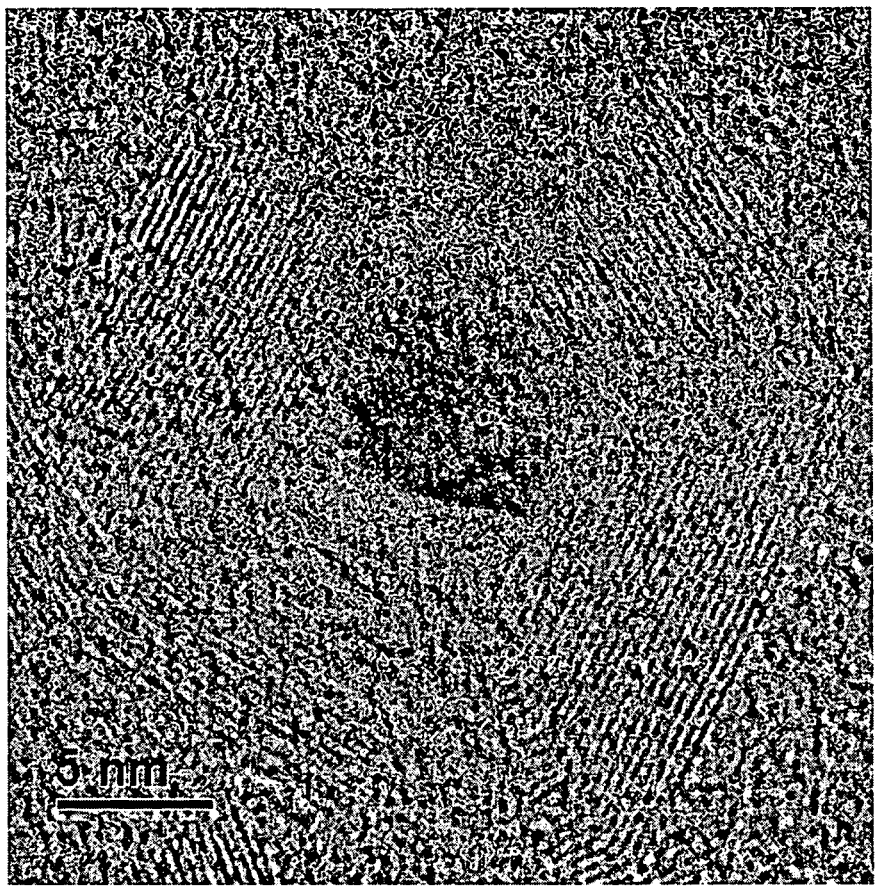
FIG. 2 is the diagram showing the reverse titration curve of quantifying the number of —COOH functional groups, and the number of —COOH measured=(66−37.375)*1 mN/10.5 mg=123 mmole/g.

The obtained product was reverse titrated by 1 mN NaOH and identified. After titration and the identification, the number of the functional group —COOH was identified about 123 mmol/g, as shown in FIG. 2.

Step 2. Forming Cis-Form Complexes of Platinum and Carbon Nanocapsules

The 2-valence Pt salts are then chelated with [C(—COOH)$_2$] group pairs to form stable cis-form complexes, as shown in FIG. 1. The detailed experiment procedures are illustrated as follows:

0.5 g of Fe@CNC—[C(COOEt)$_2$]$_n$ prepared in Example 2 was dispersed and dissolved in 10 ml of dichloromethane solvent; and then 500 mg of PtCl$_4$ was added. The mixture was substantially stirred and dissolved, and the reaction was carried on for 24 hours. A small portion of the product was drawn out and checked the contents of Pt by TGA experiment, which is 10%.

Step 3. Amination

The Cl on the product Fe@CNC—[C(COO—)$_2$PtCl$_2$]$_n$ obtained in step 2 is replaced with NH$_2$ in the present step, and Fe@CNC—[C(COO—)$_2$Pt(NH$_3$)$_2$]$_2$]$_n$, complexes will be obtained. The detailed experiment procedures are illustrated as follows:

The Fe@CNC—[C(COO—)$_2$PtCl$_2$]$_n$ obtained in step 2 was taken and subjected to reaction with NH$_3$ at a proportion of 1 ml NH$_3$ to 1 mg carbon nanocapsules. The lower the temperature, the more fully the reaction proceeds. Temperature is the key determinant of reaction rate in this regard. After drying, Fe@CNC—[C(COO—)—)$_2$Pt(NH$_3$)$_2$]$_2$]$_n$ complexes were obtained. (See FIG. 1(d)).

Step 4. Hydrolysis

Figure 3:
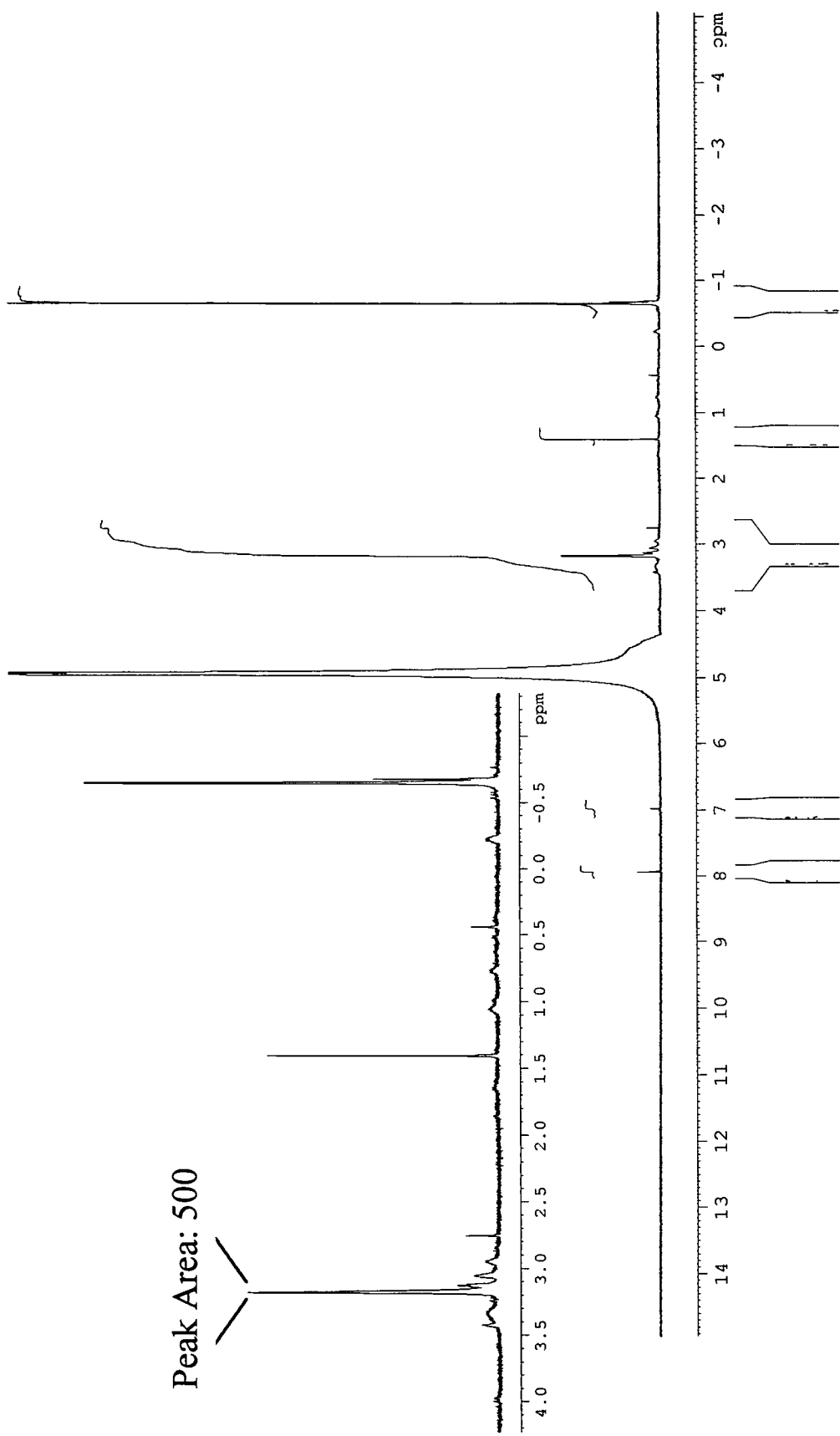
FIG. 3 is the H-NMR spectrum of the product of Example 2, which shows the product is Cis-Pt(NH$_2$)$_2$(OH)$_2$.
Figure 4:
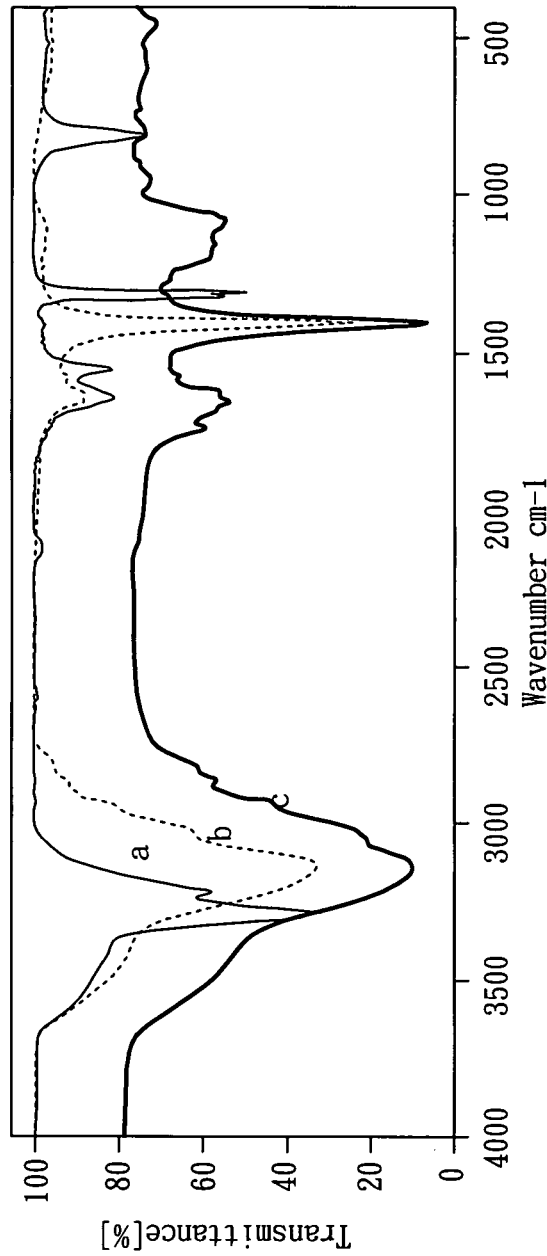
FIG. 4 is the FTIR diagram of the product of Example 2, which shows: a is standard cisplatin (provided by Phytohealth Co. ltd), b is monohydrate cisplatin obtained from hydrolysis of standard cisplatin, and c is the product Fe@CNC—[C (COOEt)$_2$]$_n$ in Example 2; comparing characteristics on FTIR diagram, it is known that the product is Cis-Pt(NH$_2$)$_2$(OH)$_2$.
Figure 5A:
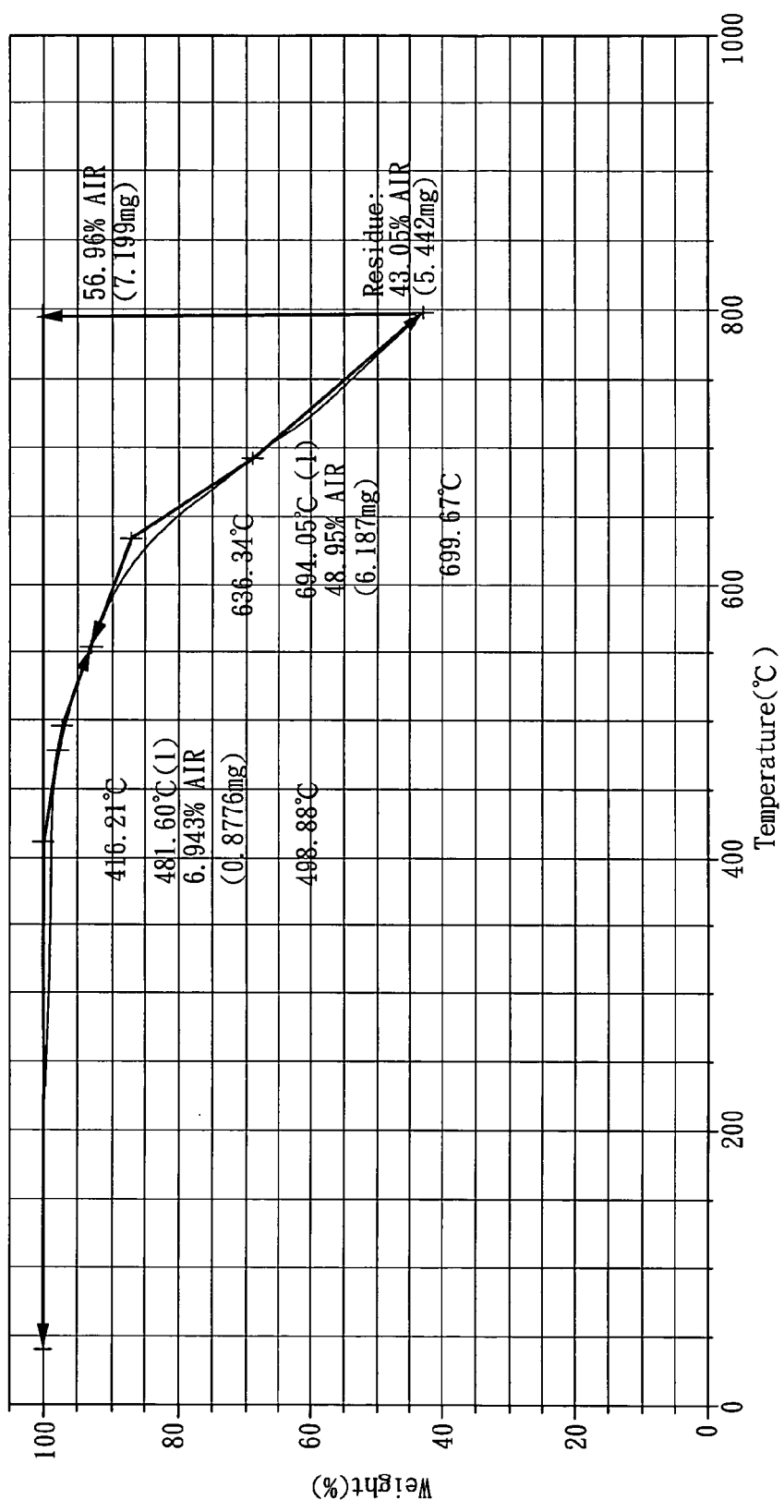
FIG. 5 is the electrospray ionization mass spectrum of the product Cis-Pt(NH$_2$)$_2$(OH)$_2$ of Example 2.
Figure 5B:
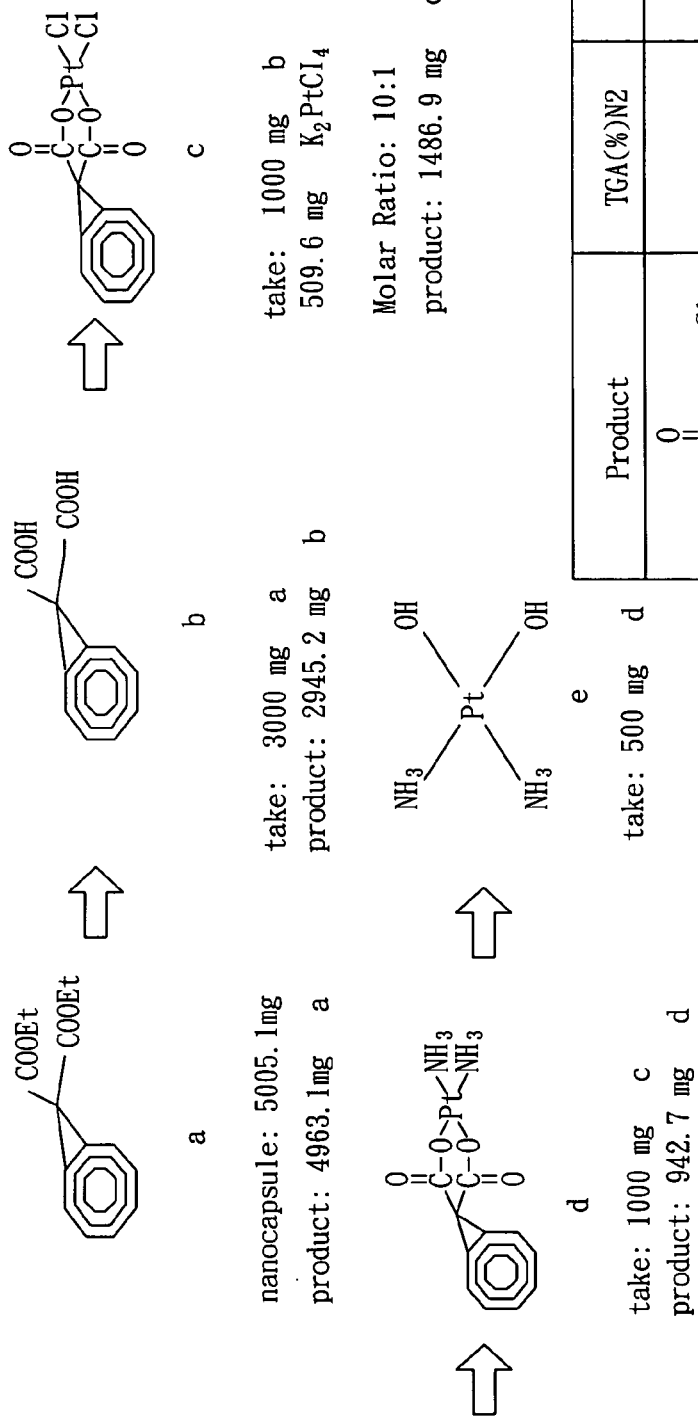

After Fe@CNC—[C(COO—)$_2$Pt(NH$_3$)$_2$]$_2$]$_n$ complexes intermediates obtained in step 3 are isolated by centrifugation, platinum in the product is removed by hydrolysis(as shown in FIG. 1). The detailed experiment procedures are illustrated as follows:

0.01N of NaOH was used as a catalyst of hydrolysis, resulting in the product Cis-Pt(NH$_2$)$_2$(OH)$_2$. The products are identified by qualitative analysis such as FTIR (FIG. 3), NMR (FIG. 3), and Electrospray Ionization Mass Spectrometry (FIG. 5). Compared with the diagrams of prior arts, the product was surely Cis-Pt(NH$_2$)$_2$(OH)$_2$.

Figure 6:
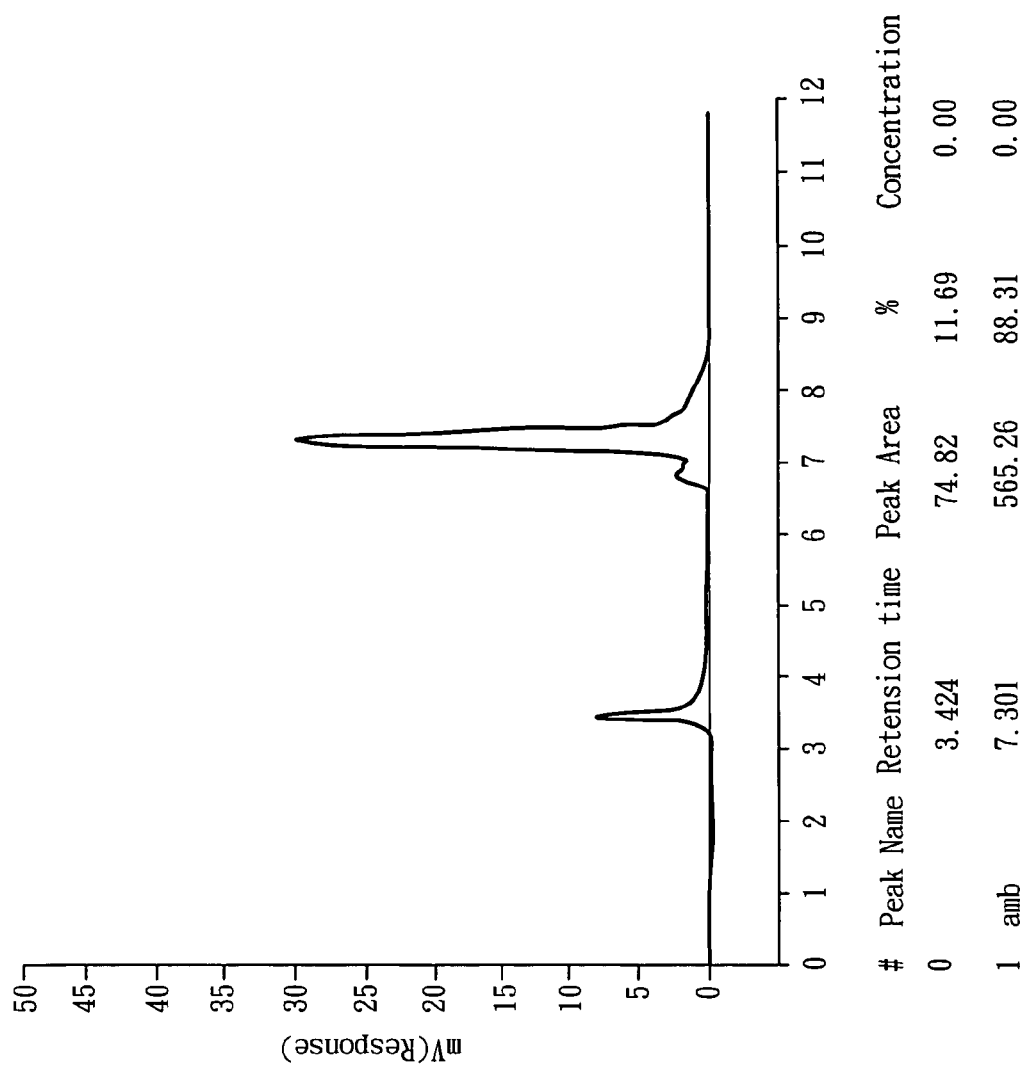
FIG. 6 shows measuring Pt contents in the product of Example 2 by a TGA test (a), and the data shows the variations of the intermediate products in different stages (Fig b illustrates the content in each step)
Figure 7:
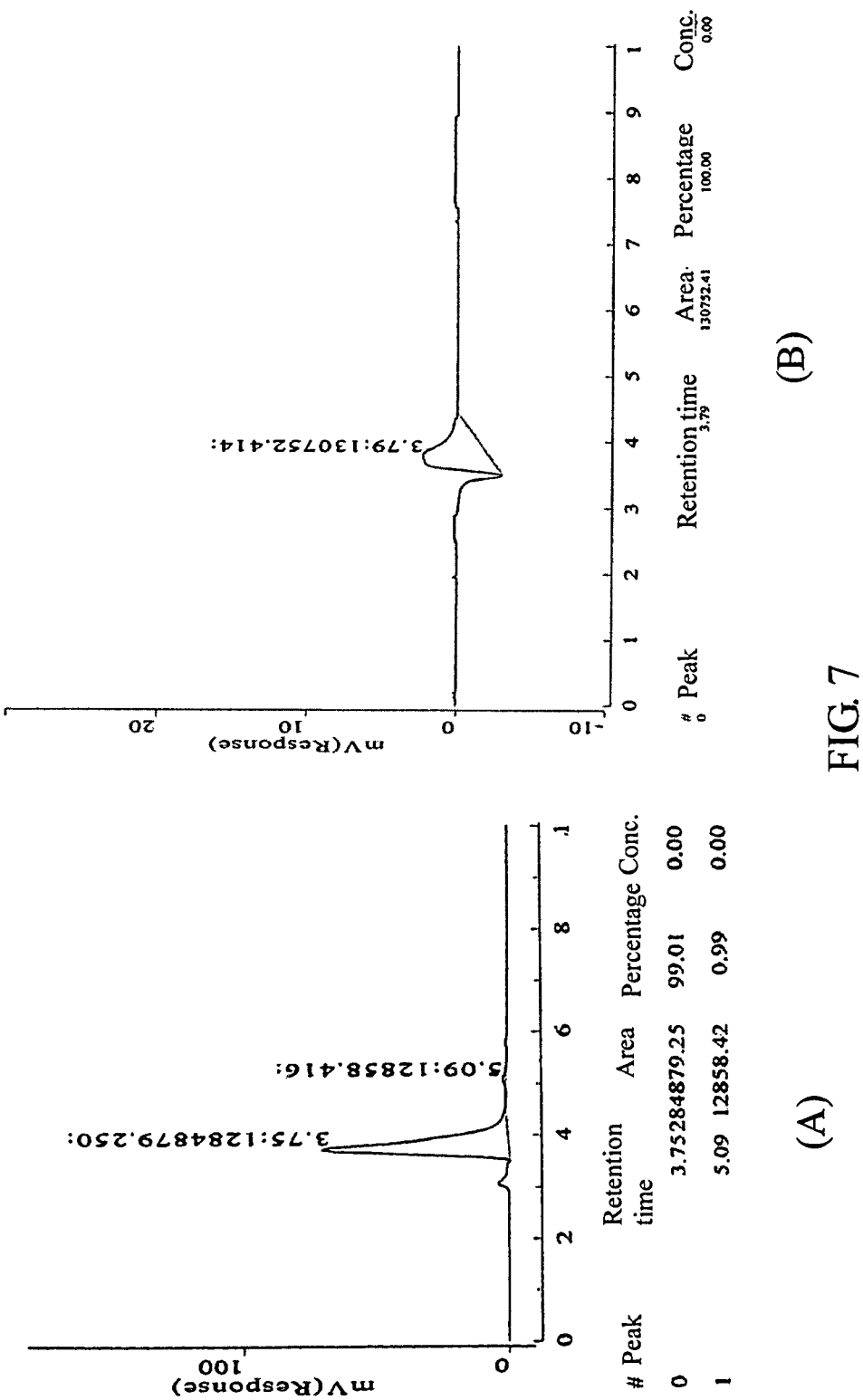
FIG. 7 is the HPLC diagram of the product of Example 2, wherein (A) is 20000 ppm of standard cisplatin, (B) is the product Cis-Pt(NH$_2$)$_2$(OH)$_2$, and the retention time and integration area of (A) and (B) are compared.

The product was subsequently subjected to quantitative analysis. From the results of TGA and HPLC experiments, the yield was about 86% (See FIG. 6, FIG. 7 and Table 1).

TABLE 1

| No. | column | Mobile phase | Flow rate (ml/min) | UV detection (nm) |
| --- | --- | --- | --- | --- |
| 1. | LichroCAR | Ammonium sulphate 0.8 g/2 L | 0.5 | 90 |
| 2. | TC18 | | 2 | 209 |
| 3. | | | 0.5 | 209 |
| 4. | YMC ODS-M80 | Ammonium sulphate 0.8 g/3 L | 2 | 209 |
| 5. | VERCOPAK | ethyl acetate/ | 0.5 | 209 |
| 6. | NUCLEOSIL | methanol/DMF/water | 0.5 | 310 |
| 7. | | Ammonium sulphate 0.8 g/2 L | 0.5 | 209 |

TABLE 1-continued

| No. | column | Mobile phase | Flow rate (ml/min) | UV detection (nm) |
|---|---|---|---|---|
| 8. | | ethyl acetate/ methanol/ DMF/water | 0.5 | 310 |
| 9. | | Ammonium sulphate 0.8 g/2 L | 0.5 | 310 |

Example 3

The Fe@CNC—[C(COO—)$_2$Pt(NH$_3$)$_2$]$_2$]$_n$ complex intermediates obtained in step 3 of Example 2 were dispersed in 0.01N HCl solution and then refluxed at high temperature for 6 hours. A plain yellow solution and black nanocapsules were obtained after separation of solid and liquid phased by magnetic-field absorption. The pH of the plain yellow solution was adjusted to 7 with NaOH solution. Water of the yellow solution was dried out by decompression, and the resultant dried yellow powder was a mixture of cisplatin and salts. The mixture was dissolved in acetone and a process of extraction was performed to obtain a yellow product. Then, the yellow product was dried, and analyses were performed on the dried yellow product.

Figure 8:
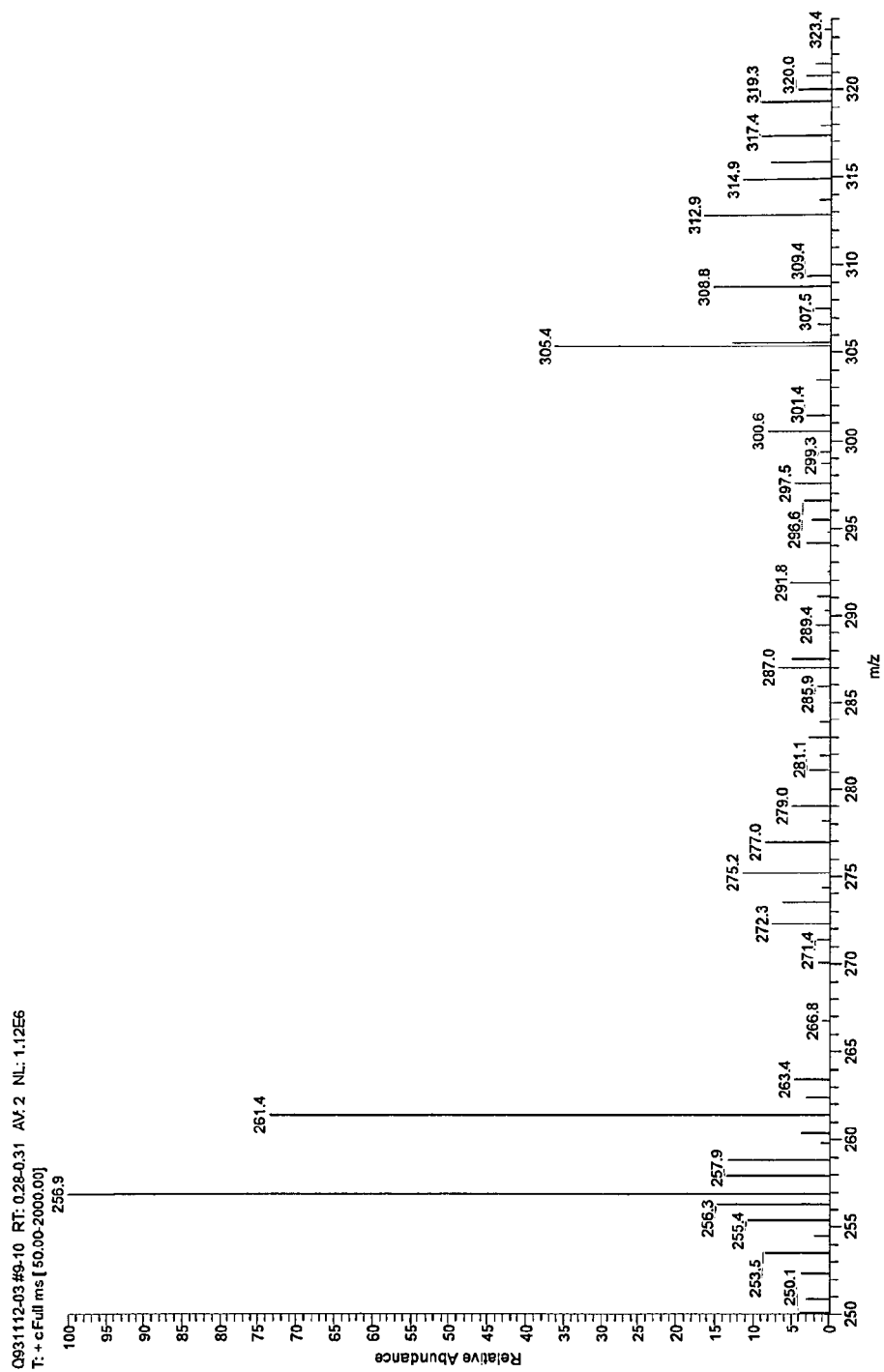
FIG. 8 is the electrospray ionization mass spectrum of the product of Example 2.
Figure 9:
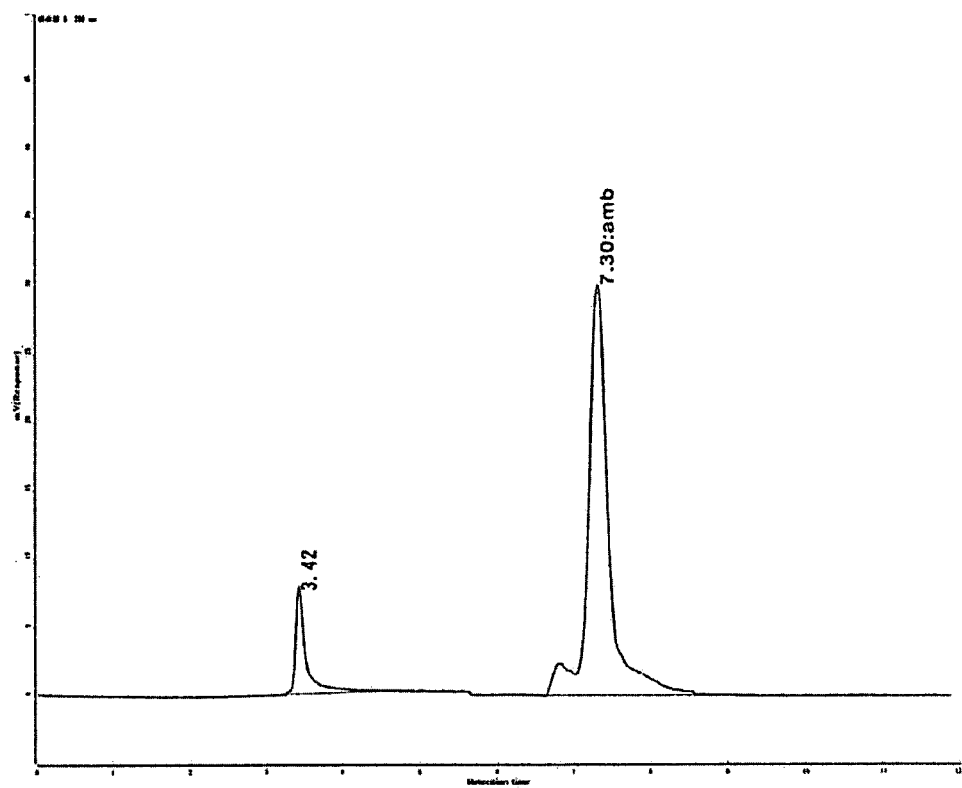
FIG. 9 is HPLC analysis, and HPLC diagrams of standard cisplatin and the synthesized product of equal concentrations are compared; the retention time of the product of Example 2 is equal to standard cisplatin, and purity is also fairly equal.
Figure 10:
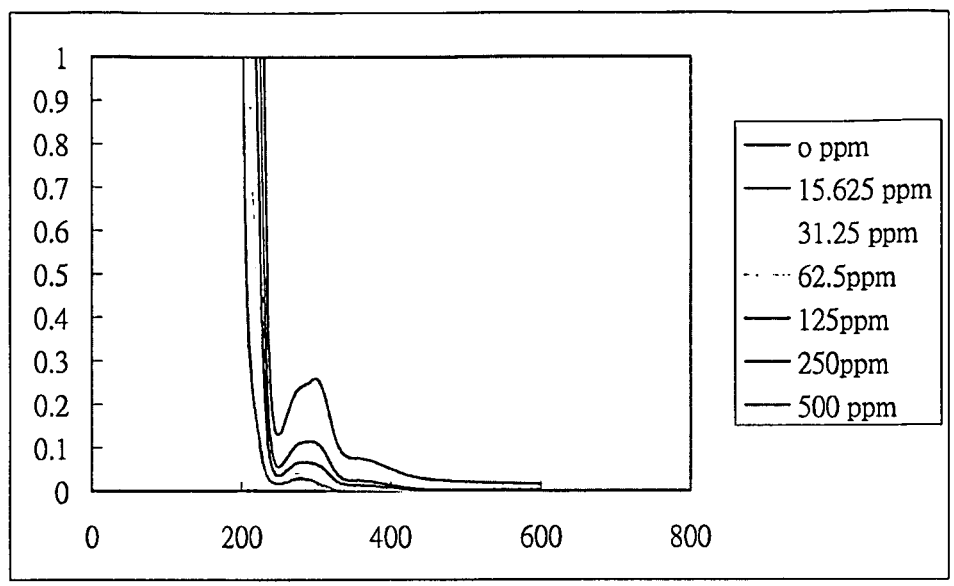
FIG. 10 is the quantity analysis of UV/VIS microscopy, wherein the absorption peak of the product of Example 2 is the same as the absorption peak of 500 ppm of standard cisplatin, so the concentraion of cisplatin in the product of Example 2 is about 4111 ppm, and the yield of product of Example 2 is 88%.
Figure 10:
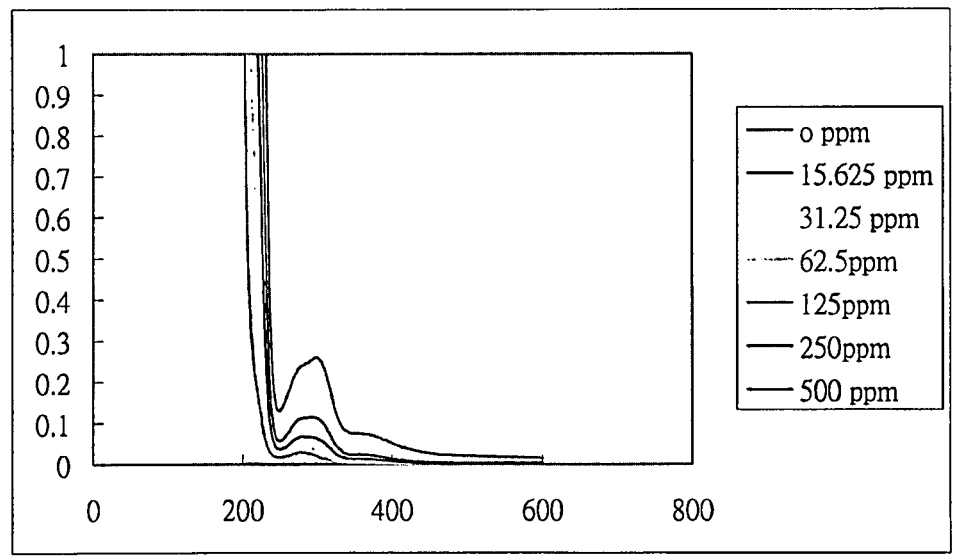

The process of the present example is the same as that of example 2, except that 0.1 N of HCl was used as a catalyst of hydrolysis, and the product of the present invention is Cis-Pt (NH$_2$)$_2$(Cl)$_2$. The product was analyzed by Electrospray Ionization Mass Spectrometry, and the result was showed in FIG. 8. Compared with the spectrum of standard cisplatin, the product of the present example is cis-form Cis-Pt(NH$_2$)$_2$(Cl)$_2$. After the product was analyzed by HPLC, UV, and TGA quantitative analyses, and the obtained results were shown in FIGS. 9 and 10. After calculation, the yield of product of the present example is about 80%.

The method of the present invention using magnetic carbon nanocapsules to prepare Cisplatin mainly employs magnetic nanocapsules as carriers. The design not only makes PtCl$_4$ material recyclable and reusable, but endows steric-selective functions that make product exclusively cis-form. Thus, the synthesis procedures are simpler than those known in the art, and the yield of Cisplatin can reach up to 80 mol %.

Although the present invention has been explained in relation to its preferred embodiment, it is to be understood that many other possible modifications and variations can be made without departing from the scope of the invention as hereinafter claimed.

What is claimed is:

1. A method for producing a drug selected from the group consisting of cisplatin and dihydrate cisplatin, in a yield of up to 80 mol %, comprising:
    (1) reacting magnetic particle-containing carbon nanocapsules having a diameter in the range of 30-40 nm, the magnetic particles comprising Fe, Co, Ni or an alloy thereof, with an effective amount of a reagent to modify the surface of the nanocapsules to provide >C(—COOH)$_2$ functional groups thereon;
    (2) reacting said >C(—COOH)$_2$ functional groups with platinum cations to bind the platinum cations to the >C(—COOH)$_2$ functional groups and form stable cis-form platinum complexes on said nanocapsules;
    (3) aminating the stable cis-form platinum complex nanocapsules by reacting said nanocapsules with ammonia to form an aminated cis-form platinum nanocapsule complex; and
    (4) hydrolyzing the aminated cis-form platinum nanocapsule complex to form cisplatin or dihydrate cisplatin;
    wherein the magnetic particle-containing carbon nanocapsule is a polyhedral carbon cluster composed of an outer shell having an enclosed multilayer graphite structure containing the magnetic particles inside; the number of functional groups—COOH is 123 mmol/g; and the surface modifying reagent is diethylbromomalonate.

* * * * *